United States Patent [19]

Gross et al.

[11] Patent Number: 5,242,406
[45] Date of Patent: Sep. 7, 1993

[54] LIQUID DELIVERY DEVICE PARTICULARLY USEFUL FOR DELIVERING DRUGS

[75] Inventors: Joseph Gross, Moshav Mazor; Shlomo Zucker, Mihmoret, both of Israel

[73] Assignee: Sil Medics Ltd., Petach Tikva, Israel

[21] Appl. No.: 809,195

[22] Filed: Dec. 16, 1991

Related U.S. Application Data

[63] Continuation-in-part of Ser. No. 599,917, Oct. 19, 1990, Pat. No. 5,090,963.

[30] Foreign Application Priority Data

| Dec. 31, 1990 | [IL] | Israel | 96835 |
| Mar. 6, 1991 | [IL] | Israel | 97457 |
| Aug. 21, 1991 | [IL] | Israel | 99262 |

[51] Int. Cl.$^5$ .................................. A61M 37/00
[52] U.S. Cl. ............................ 604/132; 222/95; 222/494; 128/DIG. 12; 604/141; 604/145
[58] Field of Search ............... 604/132–134, 604/891.1, 135–148, 153; 128/DIG. 12; 222/95, 491, 494, 386.5

[56] References Cited

U.S. PATENT DOCUMENTS

| 2,387,598 | 10/1945 | Mercier | 222/386.5 |
| 2,761,445 | 9/1956 | Cherkin | 222/96 |
| 3,115,280 | 12/1963 | Battista | 222/95 |
| 3,468,308 | 9/1969 | Bierman | 222/96 |
| 3,677,444 | 8/1972 | Merrill | 222/135 |
| 3,894,538 | 7/1975 | Richter | 222/95 |
| 3,902,638 | 9/1975 | Gillespie | 222/386.5 |
| 4,668,231 | 5/1987 | de Vries et al. | 604/891 |
| 4,741,736 | 5/1988 | Brown | 604/134 |
| 4,781,688 | 11/1988 | Thoma et al. | 604/132 |
| 4,820,273 | 4/1989 | Reinicke | 604/141 |
| 4,842,598 | 6/1989 | Tran | 604/891.1 |
| 4,886,514 | 12/1989 | Maget | 604/891.1 |
| 4,902,278 | 2/1990 | Maget et al. | 604/132 |
| 4,921,135 | 5/1990 | Pleet | 222/95 |
| 4,955,512 | 9/1990 | Sharples | 222/386.5 |
| 4,968,301 | 11/1990 | di Palma et al. | 604/132 |
| 5,007,556 | 4/1991 | Lover | 222/386.5 |
| 5,085,656 | 2/1992 | Polaschegg | 604/891.1 |
| 5,090,963 | 2/1992 | Gross et al. | 604/132 |
| 5,179,982 | 1/1993 | Berube et al. | 222/95 |

FOREIGN PATENT DOCUMENTS

0112585 4/1984 European Pat. Off. .

Primary Examiner—Randall L. Green
Assistant Examiner—G. Gualtieri
Attorney, Agent, or Firm—Benjamin J. Barish

[57] ABSTRACT

A delivery device for delivering a liquid containing a drug includes a first diaphragm within a housing defining a first contractible-chamber on one side of the diaphragm for holding a supply of the liquid to be delivered, and a second contractible chamber on the opposite side of the diaphragm including an electrolytic cell capable of generating a gas according to the electrical current passed through the cell electrolyte. The device further includes a second diaphragm, a control valve, and a spring, for compensating the rate of delivery of the liquid for variations in ambient pressure and temperature.

16 Claims, 6 Drawing Sheets

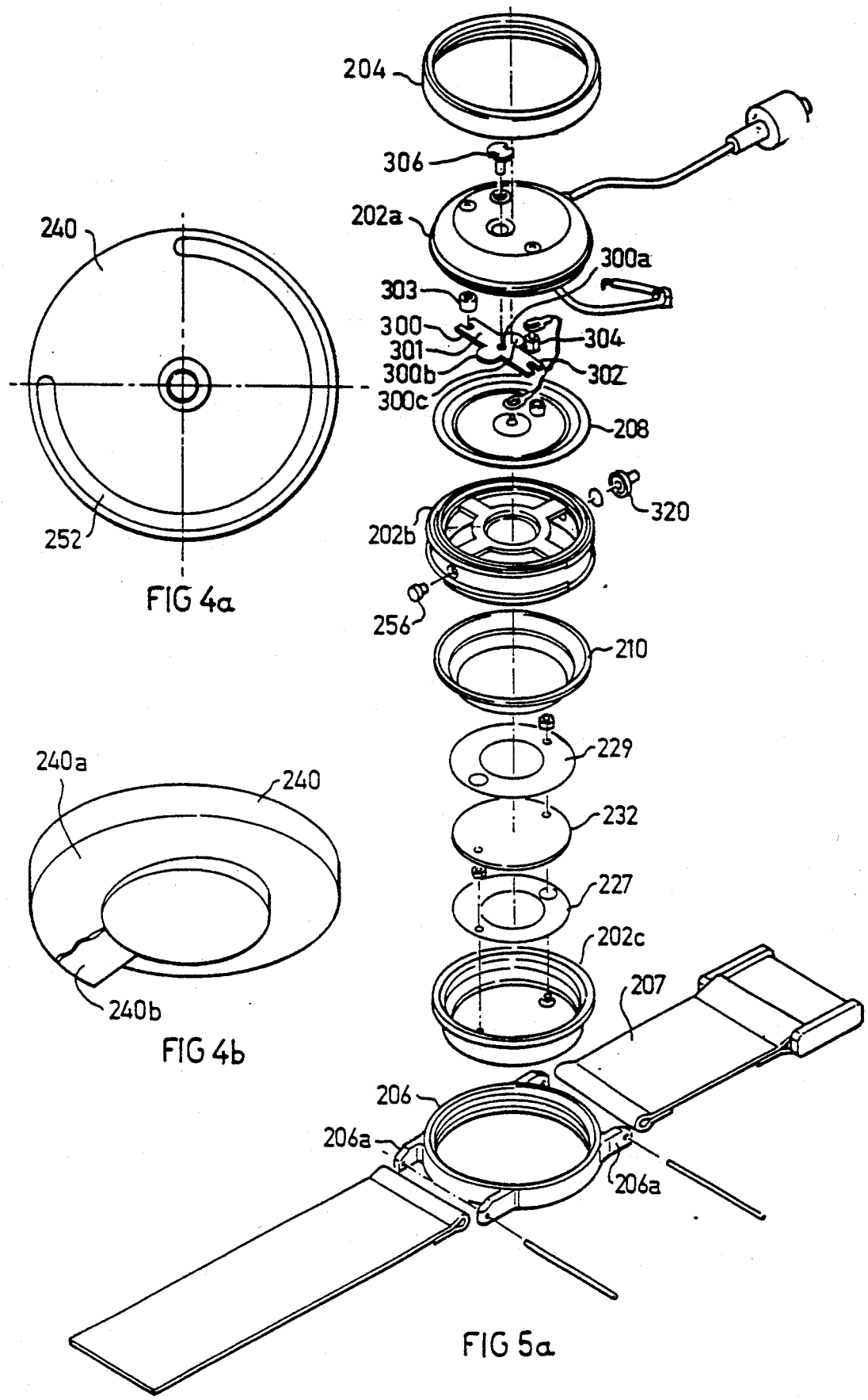

LIQUID DELIVERY DEVICE PARTICULARLY USEFUL FOR DELIVERING DRUGS

RELATED APPLICATIONS

This application is a continuation-in-part of our U.S. patent application Ser. No. 07/599,917 filed Oct. 19, 1990, now U.S. Pat. No. 5,090,963.

FIELD AND BACKGROUND OF THE INVENTION

The present invention relates to liquid delivery devices, and particularly to devices for delivering liquids containing drugs. The drugs may be in solution and/or suspension in a pharmaceutically acceptable medium which is in the liquid state under normal temperature and pressure.

Our prior U.S. Pat. No. 5,062,834 discloses a liquid delivery device including an outer housing having an outlet for the liquid to be delivered, a displaceable member within the housing defining a first contractible chamber on one side of the displaceable member for holding a supply of the material to be delivered via the outlet, and a second contractible chamber on the opposite side of the displaceable member. The device further includes pressure-control means for controlling the pressure produced in the second contractible chamber for controlling the displacement of the displaceable member, and thereby the rate of flow of the liquid via the outlet. In the device described in that patent application, the pressure-control means comprised an electrolytic cell having a pair of electrodes separated by an electrolyte capable of generating a gas applied to the second chamber according to the electrical current passing through the electrolyte.

A drawback in the device described in that patent is that the rate of flow of the liquid (e.g., a drug) via the outlet is very sensitive to variations in ambient pressure and temperature, and/or to any leakage in the pressure control chamber.

OBJECTS AND BRIEF SUMMARY OF THE INVENTION

An object of the present invention is to provide a liquid delivery device, particularly one for delivering a drug, having advantages in one or more of the above respects.

According to the present invention, there is provided a liquid delivery device as described above, characterized in that the housing further includes a second displaceable member defining a third contractible chamber between the housing and the first contractible chamber, the third contractible chamber including compensating means for compensating the rate of flow of the liquid via the outlet in response to changes in temperature and pressure.

BRIEF DESCRIPTION OF THE DRAWINGS

The invention is herein described, by way of example only, with reference to the accompanying drawings, wherein:

FIGS. 4a and 4b are top and perspective views, respectively, of the calibrating disc used in the device of FIG. 4;

FIG. 5a is an exploded view of the device of FIG. 5;

DESCRIPTION OF PREFERRED EMBODIMENTS

Figure 1:
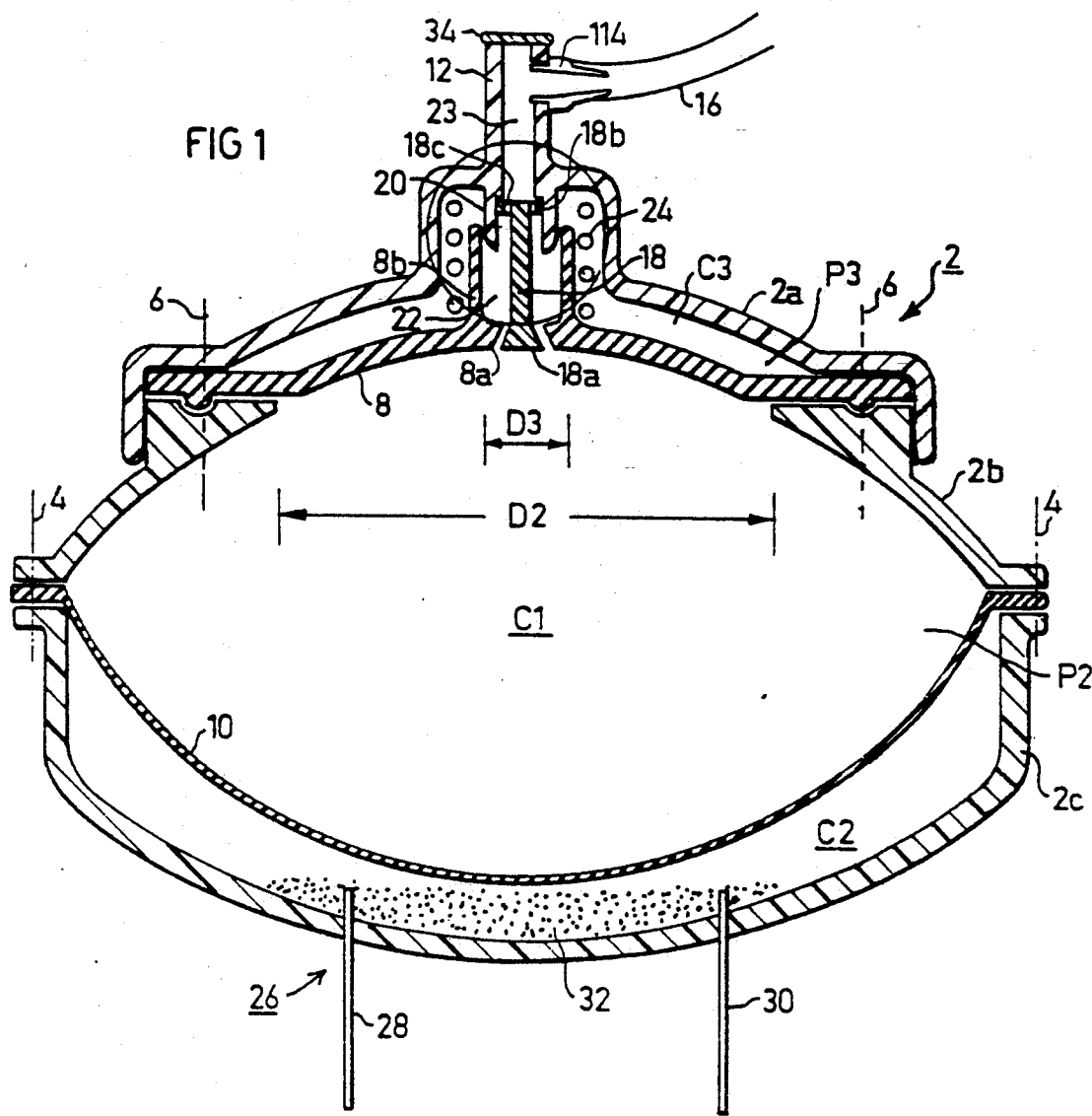
FIG. 1 is a longitudinal sectional view illustrating one form of drug delivery device constructed in accordance with the present invention.
Figure 1A:
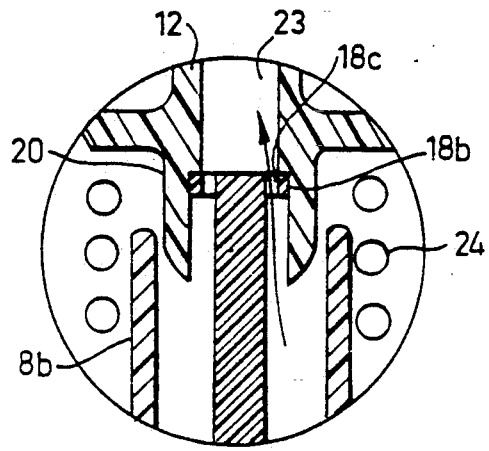
FIG. 1a being an enlarged fragmentary view of a portion of the device of FIG. 1.

The Embodiment of FIGS. 1 and 1a

The drug delivery device illustrated in FIG. 1 includes an outer rigid housing, generally designated 2, constituted of three sections 2a, 2b, 2c, all secured together in any suitable manner, e.g., by fasteners 4 and 6. The three housing sections 2a, 2b, 2c are preferably of circular cross-section. A first diaphragm 8 is clamped between housing sections 2a and 2b, and a second diaphragm 10 is clamped between housing sections 2b and 2c.

It will be seen that diaphragm 10 divides the interior of housing 2 into a first contractible chamber $C_1$ on one side of the diaphragm, and a second contractible chamber $C_2$ on the opposite side of the diaphragm; and that diaphragm 8 defines a third contractible chamber $C_3$ between it and housing section 2a. As will be described more particularly below, chamber $C_1$ serves to hold a supply of the liquid (e.g., containing a drug) to be delivered; chamber $C_2$ serves as a pressure-control chamber for controlling the rate of delivery of the drug; and chamber $C_3$ serves as a compensating chamber for reducing the sensitivity of the delivery rate to variations in ambient pressure and temperature.

Housing section 2a is formed with a tubular extension 12 having an outlet opening 14 adapted to receive a flexible tube 16 for delivering the drug to a subject. A stem 18 is fixed to the tubular extension 12 and extends inwardly into chamber $C_1$ through an opening 8a in diaphragm 8. The inner tip of stem 18 is formed with a conical head 18a, and the opening 8a through diaphragm 8 is of a complementary conical configuration, such that this opening, together with conical head 18a of stem 18, serves as a control valve between chamber $C_1$ and the outlet tube 16 connected to the subject.

Tubular extension 12 includes an inwardly-extending section 20 to which the inner end 18b of stem 18 is fixed. Diaphragm 8 is further formed with a tubular section 8b enclosing section 20 to define a passageway 22 for the liquid leaving chamber $C_1$. The fixed end 18b of stem 18 is formed with openings, as shown at 18c in FIG. 1a, to permit the liquid to flow through passageway 23 within the tubular extension 12, and from there to the outlet 14. The valve formed by stem head 18a and diaphragm opening 8a is biassed to its closed condition by a coiled spring 24 within chamber $C_3$ and interposed between diaphragm 8 and housing section 2a adjacent its tubular extension 12.

As indicated earlier, chamber $C_2$ between diaphragm 10 and housing section 2c serves as a pressure-control chamber for controlling the displacement of diaphragm 10, and thereby the rate of flow of the liquid from chamber $C_1$ to the outlet 14. For this purpose, chamber $C_2$ includes an electrolytic cell, generally designated 26, having a pair of electrodes 28, 30 separated by an electrolyte 32 capable of generating a gas within chamber $C_2$ according to the electrical current passing through the electrolyte. The electrolyte 32 is disposed within chamber $C_2$, whereas the electrodes 28, 30 pass outwardly through housing section 2c to enable them to be connected to an external electric supply, e.g., a battery.

The end of the tubular extension 12 formed with the outlet 14 is closed by a semi-permeable cap 34 which is permeable to gas, but not to liquids. Cap 34 serves to vent to the atmosphere any gas in chamber $C_1$, and thereby prevents gas from being included in the drug delivered via outlet 14 to the subject.

The drug delivery device illustrated in FIGS. 1 and 1a operates as follows:

Chamber $C_1$ is first completely filled with the liquid containing the drug to be dispensed. When the drug is to be delivered, electrodes 28, 30 are connected to a power supply (e.g., a battery), and electric current is applied thereby to the electrolyte 32 within chamber $C_2$, which electrolyte generates a gas according to the magnitude of the electric current applied. The gas generated in chamber $C_2$ displaces diaphragm 10 inwardly, thereby forcing out liquid from chamber $C_1$, via valve opening 8a in diaphragm 8, at a rate corresponding to the rate of gas generation in chamber $C_2$. The dispensed liquid flows via passageways 22 and 23 to the outlet tube 16.

As indicated earlier, the rate of delivery of the liquid from chamber $C_1$ is affected, not only by the rate of gas generation within chamber $C_2$, but also by the ambient temperature and pressure prevailing at the time the device is operated. The variations of temperature and pressure are compensated for in the device illustrated in FIG. 1 in the following way:

The variations in temperature substantially affect both sides of diaphragm 8 in the same manner; thus, an increase in temperature with respect to chamber $C_1$, tending to displace diaphragm 8 in the direction of increasing the size of the valve opening 8a, will also be applied to the opposite side of diaphragm 8 tending to decrease the size of the valve opening, thereby substantially cancelling the effects of temperature variations.

The variations in pressure will affect only the portion ($D_3$) of diaphragm 8 exposed to the atmospheric pressure via the outlet 14. However, since the complete diaphragm diameter ($D_2$) is much greater than portion $D_3$, the variations in pressure will thus have little affect in changing the flow rate via the valve opening 8a.

The semi-permeable cap 34 at the end of the extension tube 12 vents gas to the atmosphere but not liquid. Accordingly, should gas enter chamber $C_1$ (e.g., because of a leakage, or a rupture of diaphragm 10), such gas will be vented via cap 34 and therefore will not be included in the drug delivered to the subject via outlet 14. Cap 34 may also be used for initially priming the pump.

Figure 2:
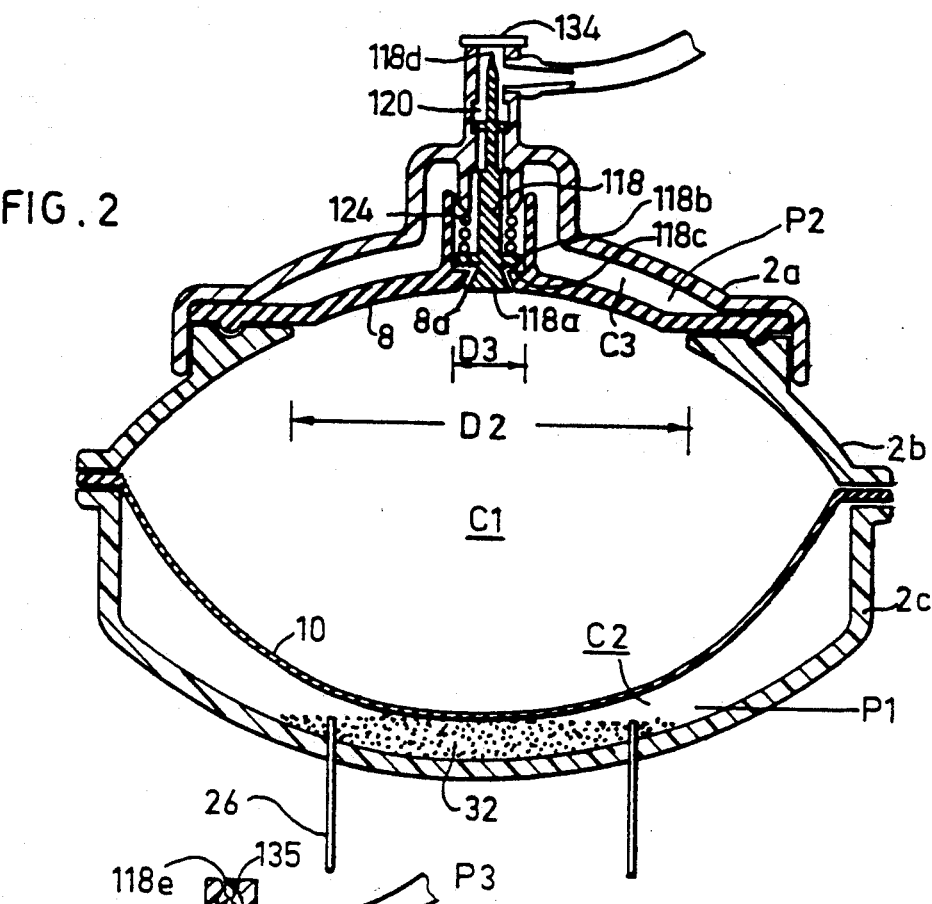
FIGS. 2, 3, 4 and 5 are longitudinal sectional views illustrating four further forms of drug delivery devices constructed in accordance with the present invention.

The Embodiment of FIG. 2

The drug delivery device illustrated in FIG. 2 is constructed and operates in a substantially similar manner as described above with respect to FIG. 1; to facilitate understanding, its parts which are generally the same as those in FIG. 1 are identified by the same reference numerals.

In the drug deliver device illustrated in FIG. 2, the stem, identified as 118, includes a conical head 118a serving as the valve member cooperable with valve opening 8a in diaphragm 8, in the same manner as described above with respect to FIG. 1. Stem 118, however, is integrally formed with an annular ring 118b serving as a shoulder for the spring 124, which spring biasses ring 118b towards diaphragm 8. The underface of ring 118b is formed with ribs 118c, to permit liquid from chamber $C_1$ to flow into passageway 120 to the outlet 114.

The opposite end 118d of stem 118 is pointed and is normally spaced from the venting cap 134. In this case, the venting cap 134 is of a material which is pierceable by the stem pointed end 118d upon the excessive displacement of the stem.

Thus, spring 124 and diaphragm 8 will reduce the sensitivity of the delivery device to variations in temperature and pressure in the same manner as described above with respect to FIG. 1.

In addition, should the supply of the drug within chamber $C_1$ becomes exhausted, or should an excessive pressure be otherwise produced in chamber $C_1$ (e.g., by an occlusion downstream of the outlet 114), stem 118 will be displaced so that its pointed end 118d pierces cap 134, thereby causing the drug within the passageway 120 to flow out through the vent, rather than via the outlet 114.

Figure 3:
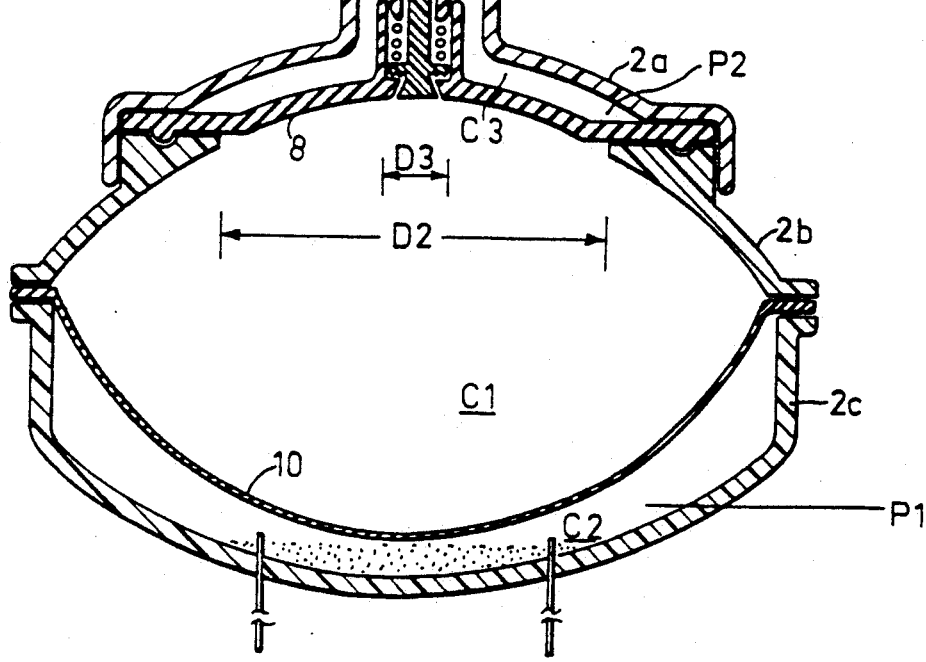

The Embodiment of FIG. 3

FIG. 3 illustrates a construction very similar to that of FIG. 2, and therefore its parts are identified by the same reference numerals. In the construction of FIG. 3, however, cap 134 is replaced by a second valve including a valve opening, identified as 135, formed in the extension 12 (instead of in cap 134), cooperable with the end of valve stem 118. Valve stem 118 is formed with a tip 118e which, during the normal operation of the device, is located in valve opening 135 to close the vent, but upon the excessive displacement of stem 118, positions an annular recess 118f within opening 135, thereby opening the vent.

In all other respects, the drug delivery device illustrated in FIG. 3 is constructed and operates in the same manner as described above.

Figure 4:
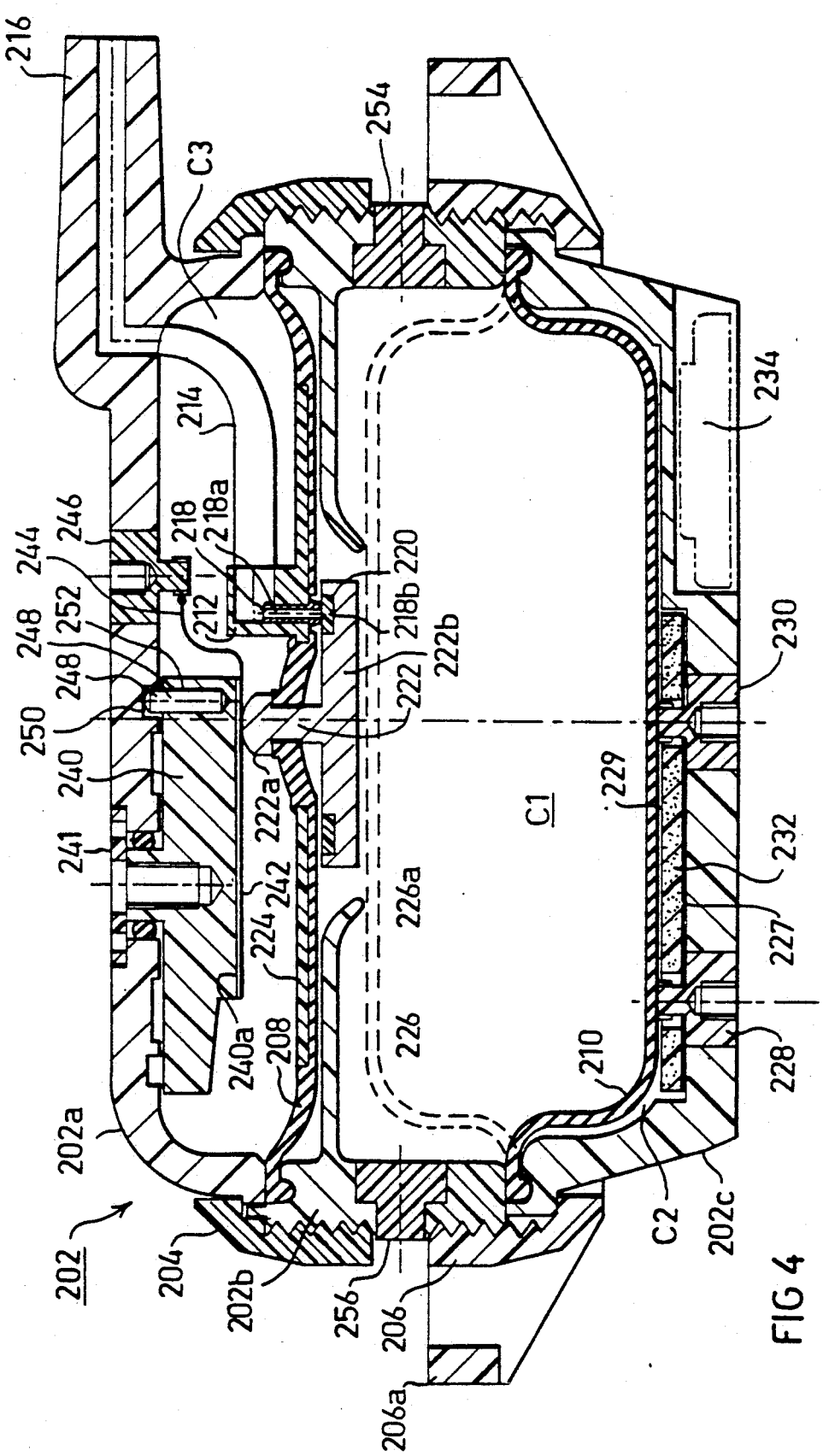

The Embodiment of FIG. 4

FIG. 4 illustrates another form of drug delivery device constructed in accordance with the present invention but provides a number of additional features as compared to the devices of FIGS. 1-3.

Thus, the device illustrated in FIG. 4 also includes an outer rigid housing 202 constituted of three sections 202a, 202b, 202c secured together by a pair of bevel rings 204, 206. Bezel ring 206 is provided with extensions 206a at its opposite ends to receive a wrist band and thereby to permit the device to be worn on the wrist of the user. A diaphragm 208 is clamped between housing sections 202a and 202b, and a second diaphragm 210 is clamped between housing sections 202b and 202c. The two diaphragms 210 and 208 divide the interior of housing 202 into a liquid (e.g., drug) containing chamber $C_1$, a pressure-control chamber $C_2$ and a compensating chamber $C_3$, as in the previously-described embodiments.

Diaphragm 208 carries a fitting 212 connected by a flexible tube 214 to an outlet opening 216 through which the drug is delivered to a subject. Fitting 212 further includes a valve member 218 formed with an axial bore 218a and a conical head 218b engageable with a valve seat 220. The valve seat 220 is of annular configuration fixed to a metal stem 222 carried by the central portion of diaphragm 208. Stem 222 is formed with an enlarged head 222a disposed within the compensating chamber $C_3$, and with a disc section 222b located in the drug chamber $C_1$.

Seat 220 is carried on the upper surface of disc section 222b of stem 222 in alignment with valve member 218. Fitting 212 carrying the valve member is integrally formed with a rigid annular member 224 fixed to the upper surface of diaphragm 208, and serves to stiffen the diaphragm. Housing section 202b is integrally formed with an annular member 226 underlying diaphragm 208 to limit the displacement of the diaphragm. The central part of annular member 226 is turned inwardly into compartment $C_1$ below the outer face of disc 222b of the stem 222, to prevent the lower diaphragm 210 from engaging the underface of the disc.

Chamber $C_2$, between diaphragm 210 and housing section 202c, contains an electrolytic cell having a pair of electrodes 227, 229 having terminals 228, 230 and separated by an electrolyte 232 capable of generating a gas within chamber $C_2$ according to the electrical current passing through the electrolyte. Housing section 202c, through which the two electrodes 228, 230 pass, may also be formed with a compartment 234 for receiving one or more batteries to energize the electrolytic cell.

A calibrating member 240 is carried by housing section 202a and cooperates with stem 222 carried by diaphragm 208. Calibrating member 240 is in the form of a disc which may be rotated by a screw 241. The lower surface of calibrating disc 240 is cut with a helical rib 240a of increasing thickness (FIG. 4b) engaged by the head 222a of stem 222, such that rotating the calibrating disc 240 by screw 241 will displace the stem with respect to diaphragm 208 more or less into the drug chamber $C_1$.

Calibrating screw 241 and disc 240 are preferably made of metal so as to provide electrical continuity to the underface of the disc. A layer of a pressure-sensitive resistor material 242, such as a silicone rubber-graphite composition, is carried by the helical rib 240a of the calibrating disc 240. The calibrating screw 241 serves as one terminal of an electrical circuit which includes the metal calibrating disc 240 and the layer 240b of pressure-sensitive resistor material. Layer 240b is connected by an electrical conductor 244 to another electrical terminal 246 of the electrical circuit.

The rotation of calibrating disc 240 is guided by a pin 248 having one end received within a recess 250 formed in housing section 202a, and the opposite end received within an annular groove 252 (FIG. 4a) formed partially around the circumference of the calibrating disc.

Housing section 202b further includes a drug-injection port 256 for injecting a drug into chamber $C_1$, and vent 254, such as a hydrophobic filter, which is permeable to air but not to liquid.

The device illustrated in FIG. 4 is used in the following manner:

The device is first precalibrated for a particular temperature and pressure. This may be done by applying a predetermined air pressure via the hydrophobic filter 256, and rotating the calibrating screw 242 until diaphragm 208 is displaced to open valve 218. As one example, the device may be precalibrated for 400 mm water (e.g., 0.04 atmospheres) in this manner.

The liquid drug to be delivered is then introduced into chamber $C_1$ by injection via port 254. During this introduction of the drug, the air within chamber $C_1$ is vented to the atmosphere via the hydrophobic filter 256. As soon as the pressure within chamber $C_1$ reaches the precalibrated pressure, valve 218 opens, so that liquid exits through the outlet 216. This provides an indication that the device has been primed.

In use, electrodes 228, 230 are connected to batteries 234 and cause the electrolyte 232 to generate a gas in chamber $C_2$ corresponding to the current supplied. In the event there was some pressure loss from chamber $C_1$ (e.g., because of a leakage), head 222a of the stem 222 will not be in engagement with the pressure-sensitive resistor layer 242 carried by the underside of the calibrating disc 240, and this fact will be indicated by the electrical signal outputted from the two terminals 242, 246 connected together via the pressure-sensitive layer 242 and electrical lead 244. Also, valve 218 will be closed on the valve seat 220, so that no liquid will be dispensed from chamber $C_1$.

As soon as diaphragm 208 moves the stem head 222a to contact the pressure-sensitive resistor layer 242 of the calibrating disc 240, valve member 218 opens with respect to valve seat 220 to start the delivery of liquid from chamber $C_1$. The pressure applied by stem head 222a against the pressure-sensitive resistor layer 242 reduces the resistance of that layer. An electrical signal is thus outputted between the two terminals 242, 246, indicating the start of delivery of the drug from compartment $C_1$ through the outlet 216.

In case of an overpressure occurring in the drug chamber $C_1$, such as may be caused by an occlusion in the feeding of the drug to the patient or by the exhaustion of the drug from chamber $C_1$, this will be sensed by the pressure applied by stem head 222a against the pressure-sensitive resistor layer 242. In such a case, the device could be automatically turned-off, and/or an alarm or indicator could be energized. In addition, by providing the operating pressure of the control valve always higher than the head pressure of the supply tube, the influence of the supply tube position is eliminated relative to the pump.

It will thus be seen that the amount of drug delivered via outlet 216 can be easily controlled by the electrical current applied to the two electrodes 228, 230 of the electrolytic cell including the electrolyte 232. It will also be seen that the described arrangement, particularly the stem 222 and the valve 218 both carried by the diaphragm 208, senses the actual start of delivery of the drug so that precise quantities can be delivered at precise rates.

Figure 5:
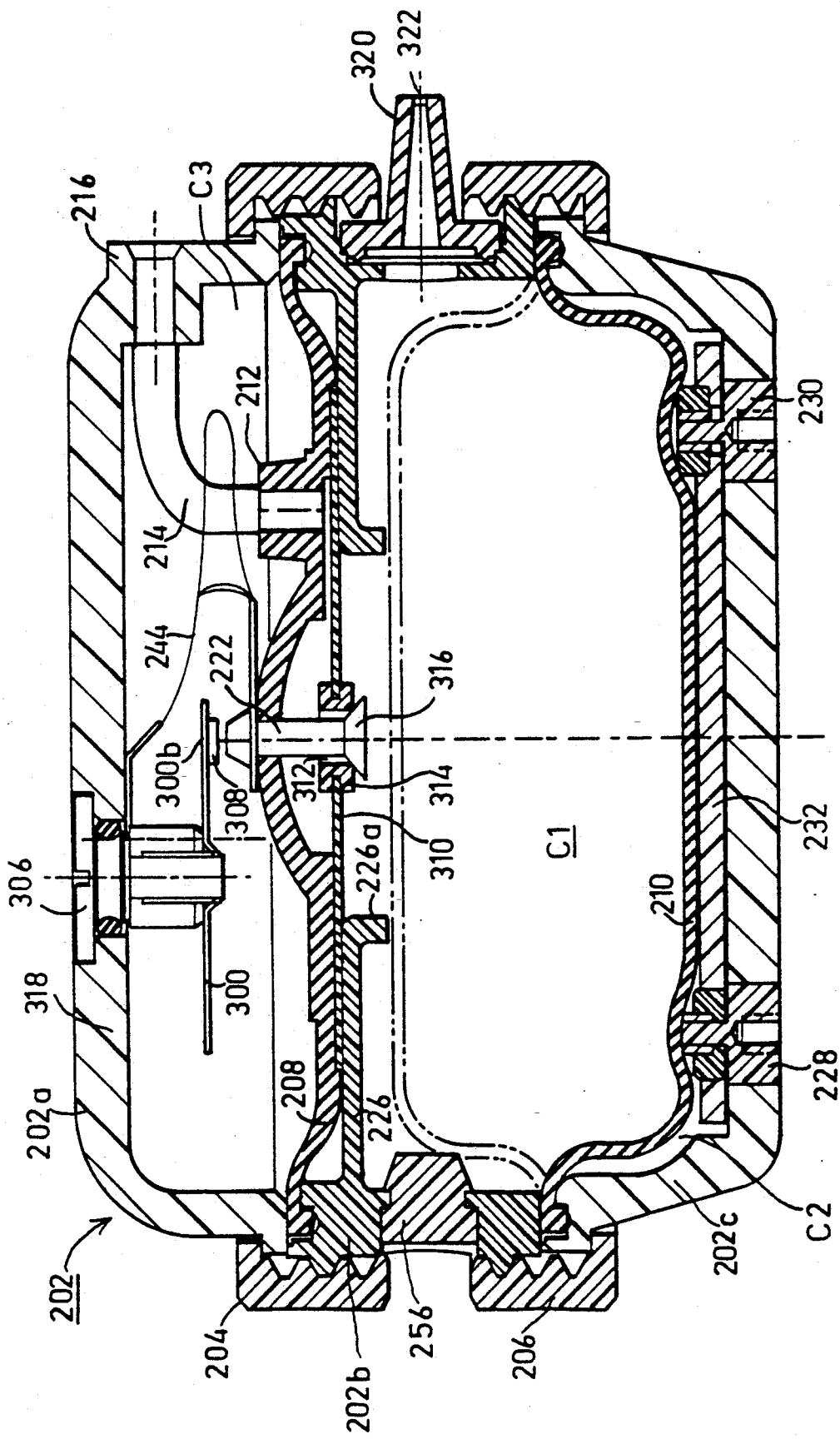

The Embodiment of FIGS. 5 and 5a

The device illustrated in FIGS. 5 and 5a is similar to that of FIG. 4, and those parts which are generally similar to those in FIG. 4 are correspondingly numbered. A main difference in the construction of the device of FIGS. 5 and 5a is in the calibrating mechanism.

Thus, instead of using a calibrating disc (240, FIG. 4), the calibrating mechanism in the device of FIGS. 5 and 5a includes a leaf spring 300 which is fixed at its opposite ends 301, 302 to the upper housing section 202a by a pair of fasteners 303, 304. A pin 306 is threaded through the upper housing section 202a and through the center 300a of the leaf spring, such that the leaf spring is bowed at its center, and its center may be moved towards and away from the upper diaphragm 208 by threading pin 306 more or less into the housing section 202a. The bowed central section of leaf spring 300 is formed with a pair of laterally-extending tabs 300b, 300c, one of which overlies the stem 222 received in the upper diaphragm 208. The tab (e.g., 300b) overlying stem 222 is provided with a layer of a pressure-sensitive resistor 308, of the same material and for the same purpose as the pressure-sensitive resistor layer 242 in FIG. 4.

Another difference in the device of FIGS. 5 and 5a, as compared to that of FIG. 4, is that a rigid reinforcing disc 310 is bonded to the undersurface of the upper diaphragm 208. The center of the rigid disc 310 is formed with an opening 312 lined with a rubber ring 314 serving as a valve seat, and stem 222 extends through opening 312 and terminates in a conical head 316 cooperable with valve seat 314.

It will thus be seen that in the device of FIGS. 5 and 5, threaded pin 306, threadedly engaging the center of the bowed leaf spring 300, serves as the calibrating means, corresponding to calibrating disc 240 in FIG. 4; and that the conical head 316 of stem 222, cooperable with valve seat 314, serves as the auxiliary valve corresponding to valve member 218 and valve seat 220 in FIG. 4. In addition, the electrical conductor 244 for sensing contact of the stem 222 with the calibrating bowed spring 300, particularly the pressure-sensitive resistor 308 on tab 300b of the spring, connects the calibrating screw 306 to the metal stem 222, and when the stem contacts the pressure-sensitive resistor 308, the circuit is completed to the bowed spring 300 connected externally by a connector shown schematically at 318 in FIG. 5.

Another minor difference in the FIGS. 5, 5a device over that of FIG. 4 is that the vent in chamber $C_1$ is in the form of a nipple 320 closed by a hydrophobic filter 322.

The device illustrated in FIGS. 5 and 5a is otherwise constructed and operates in substantially the same manner as the device of FIG. 4. As shown particularly in FIG. 5a, the bevel ring 206 may also be provided with extensions 206a on its opposite sides for receiving a band to enable wearing the device on the user's wrist.

Figure 6:
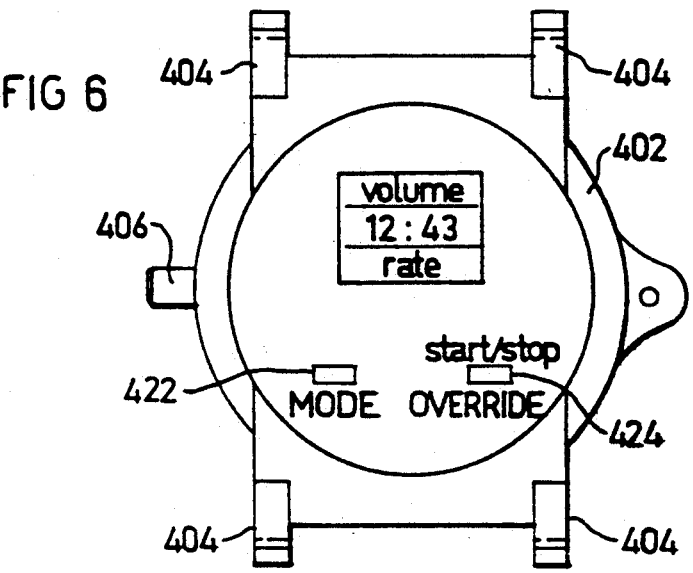
FIG. 6 is a top plan view illustrating any one of the devices of FIGS. 1-5 adapted to be worn on a wrist and including a control circuit for controlling the delivery of the drug.
Figure 7:
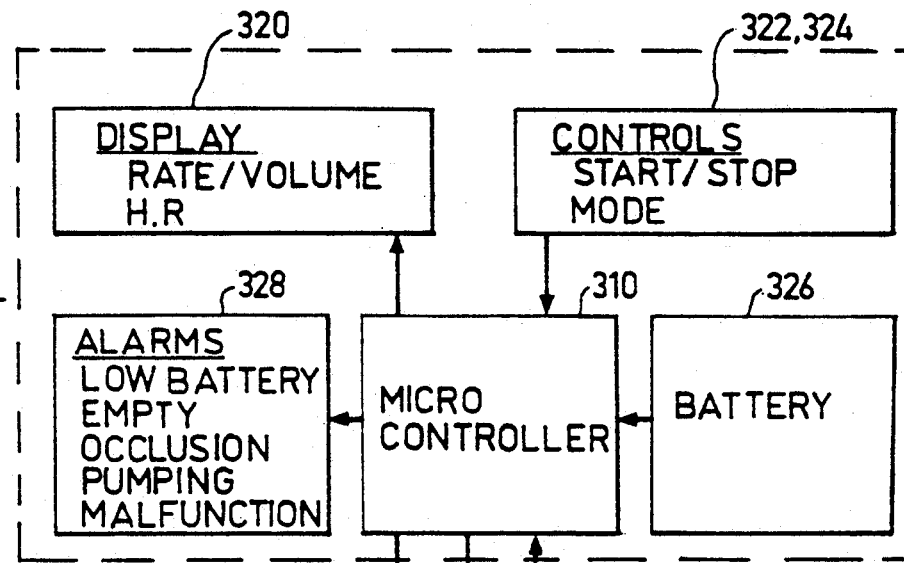
FIG. 7 is a block diagram illustrating the control circuit included in the device of FIG. 6.
Figure 7:
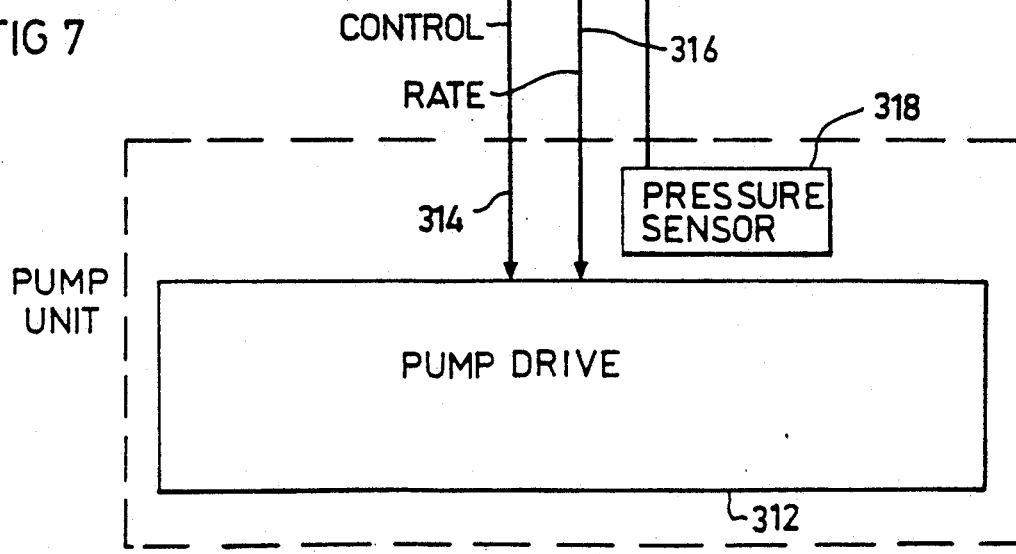

The Embodiment of FIGS. 6 and 7

FIGS. 6 and 7 illustrate an embodiment of the invention wherein the drug delivery device is equipped with an electronic control circuit which permits the drug to be delivered to the user at preprogrammed times and rates.

As shown in FIG. 6, the device includes a housing 402 also provided with extensions 404 for receiving a wrist band to enable the device to be worn on the user's wrist. The interior of housing may be constructed as described above with respect to any one of FIGS. 1-5. The housing 402 is provided with a drug delivery outlet 406, and also with a port 408 which is permeable to gas but not to liquid.

The upper part of the housing includes the electronic control circuit for controlling the time and rate of drug delivery via the outlet 406. As shown in FIG. 7, the control circuit includes a microcontroller 310 which controls the pump drive, namely the electrical current supplied to the two electrodes of the electrolytic cell to cause the electrolyte to generate the propellant gas. The start and stop signals are fed by the microcontroller 310 to the pump drive (electrolytic cell electrodes) via conductor 314, and a signal indicating the magnitude of the electrical current supplied, which determines the rate of drug delivery, is fed to the pump drive via conductor 316. The actual start of drug delivery is sensed by the pressure sensor 318 (e.g., stem head 222a engaging the pressure-sensitive layer 242 in the FIG. 4 embodiment), so that the microcontroller can keep an accurate measurement of the actual quantity of drug delivered. The volume and rate of drug delivery is displayed in a display 320 viewable on the face of the device as shown in FIG. 6. The face of the device further includes a mode switch 322 (shown at 422 in FIG. 6) which permits preprogramming the quantities and times of drug delivery, and an override start/stop switch 324 (shown at 424 in FIG. 6) to permit manual control. The device further includes a battery supply 326, an alarm 328 (e.g., visual and/or audible) to indicate various conditions such as low battery, empty, occlusion, pumping, and malfunction.

While the invention has been described with respect to several preferred embodiments, it will be appreciated that these are set forth merely for purposes of example, and that many other variations, modifications and applications of the invention may be made.

What is claimed is:

1. A liquid delivery device including:
   an outer housing having an outlet for a liquid to be delivered;
   a displaceable member within the housing defining a first contractible chamber on one side of the displacement member for holding a supply of the liquid to be delivered, and a second contractible chamber on an opposite side of the displaceable member in which a pressure is to be produced for controlling the displacement of the displacement member, and thereby the rate of flow of the liquid via said outlet;
   and pressure control means for controlling the pressure produced in said second contractible chamber;
   characterized in that said housing further includes:
   a second displaceable member defining a third contractible chamber between said housing and said first contractible chamber adjacent to said outlet;
   said third contractible chamber including compensating means for compensating the rate of flow of the liquid via said outlet in response to changes in temperature and pressure.

2. The device according to claim 1, wherein said compensating means comprises:
   a second valve between said displaceable member and said housing outlet;
   and biassing means for biassing said second displaceable member in a direction tending to close said control valve, such as to compensate the rate of flow of the liquid via the outlet for variations in ambient pressure and temperature.

3. The device according to claim 2, wherein both of said displaceable members are diaphragms, and said pressure control means comprises an electrolytic cell having a pair of electrodes separated by an electrolyte capable of generating a gas applied to said second chamber according to electrical current passing through said electrolyte.

4. The device according to claim 3, wherein the cross sectional area of the second diaphragm is many times greater than that of an outlet side of said control valve, 5. The device according to claim 2, wherein said housing includes venting means between said control valve and said outlet.

6. The device according to claim 3, wherein said third chamber includes electrical sensor means for sensing the opening of said control valve.

7. The device according to claim 6, wherein said sensor means comprises a valve member and a valve seat both carried by said second diaphragm;

said valve seat having a lost-motion connection with respect to said valve member such that the valve member is normally closed with respect to the valve seat, but upon engagement of the second diaphragm with a fixed part of the housing, the valve member moves with respect to the valve seat to open the valve to said outlet;

and electrical means for sensing the engagement of the valve member with respect to said fixed part of the housing.

8. The device according to claim 7, wherein said lost-motion connection comprises a stem carried by said second diaphragm and engageable on one side thereof with said fixed part of the housing, said valve member also being carried by said second diaphragm; said stem being displaceable with respect to said second diaphragm and carrying the valve seat on an opposite side of said second diaphragm.

9. The device according to claim 7, wherein said fixed part of the housing includes a pressure-sensor sensing the pressure applied by said stem against the fixed part of the housing.

10. The device according to claim 8, further including calibrating means for precalibrating the pressure required in said second chamber for opening said control valve.

11. The device according to claim 10, wherein said calibrating means comprises a rotatable member rotatably carried by said housing and having an inclined surface engageable with said stem carried by said second diaphragm.

12. The device according to claim 10, wherein said calibrating means comprises a leaf spring fixed at its opposite ends to the housing, and a threaded pin threaded through an opening in said housing and engageable with an intermediate portion of the leaf spring to move said intermediate portion towards or away from said opening in the housing.

13. The device according to claim 1, wherein said second chamber comprises a drug injection port for injecting a drug into said second chamber, and a vent permeable to air but not to liquid to permit priming the device.

14. The device according to claim 3, wherein the housing includes first, second and third section attachable together; said first section including said outlet and being attachable to one side of said second section, with one diaphragm clamped therebetween; the other side of said second section being attachable to said third section with the other diaphragm clamped therebetween.

15. The device according to claim 1, wherein said housing includes means for attaching the housing to a wrist of a user.

16. The device according to claim 3, wherein said housing includes an electronic control for controlling the time and magnitude of the electrical current passing through said electrolyte.

* * * * *